United States Patent [19]
Fleming

[11] Patent Number: 5,149,626
[45] Date of Patent: Sep. 22, 1992

[54] MULTIPLE ANTIGEN IMMUNOASSAY

[75] Inventor: Nigel Fleming, Arlington, Mass.

[73] Assignee: McLean Hospital Corporation, Belmont, Mass.

[21] Appl. No.: 449,158

[22] Filed: Dec. 18, 1989

Related U.S. Application Data

[63] Continuation of Ser. No. 49,375, May 14, 1987, abandoned.

[51] Int. Cl.$^5$ .................. G01N 33/53; G01N 33/537; G01N 33/543
[52] U.S. Cl. .................. 435/7.9; 435/7.92; 435/973; 435/7.1; 436/501; 436/518; 436/527; 436/528; 436/529; 436/530; 436/824
[58] Field of Search .................. 435/7, 174, 179, 181, 435/810, 973, 7.9, 7.92; 436/501, 518, 527, 528, 529, 530, 532, 824

[56] References Cited

U.S. PATENT DOCUMENTS

| | | | |
|---|---|---|---|
| 4,098,876 | 7/1978 | Piaso et al. | 424/1 |
| 4,254,096 | 3/1981 | Monthony et al. | 436/532 |
| 4,279,885 | 7/1981 | Reese et al. | 435/7 |
| 4,305,924 | 12/1981 | Piasio et al. | 436/528 |
| 4,376,110 | 3/1983 | David et al. | 436/513 |
| 4,380,580 | 4/1983 | Boguslaski et al. | 436/532 X |
| 4,427,580 | 1/1984 | Kinsella et al. | 260/112 R |
| 4,514,508 | 4/1985 | Hirschfeld | 436/531 X |
| 4,642,285 | 2/1987 | Halbert et al. | 435/7 |
| 4,693,985 | 9/1987 | Degen et al. | 436/532 X |

OTHER PUBLICATIONS

Oellerich, M., J. Clin. Chem. Clin. Biochem., vol. 22, 1984, pp. 895-904.
Pharmacia, Affinity Chromatography, Principles and Methods, printed in Sweden by Ljungföretagen AB, 1986, pp. 72, 87, 93.
Dodd et al., Biological Abstracts, 70:2479 (1980).
Hirano et al., Anal. Biochem., 154:624-631 (1986).
Handman et al., J. Immunol. Meth., 83:113-123 (1985).
Suresh et al., Anal. Biochem., 151:192-195 (1985).
Sandwick et al., Anal. Biochem., 147:210-216 (1985).
Mosbach, K., Ann. N.Y. Acad. Sci., 434:239-248 (1984).
Monroe, BioTechniques, 3:222-224 (1985).
Freeman et al., J. Immunol. Meth., 78:259-265 (1985).

Primary Examiner—Esther L. Kepplinger
Assistant Examiner—Toni R. Scheiner
Attorney, Agent, or Firm—Sterne, Kessler, Goldstein & Fox

[57] ABSTRACT

The invention relates to an assay for one or more analytes which comprises contacting a sample suspected of containing one or more analytes with a solid phase containing one or more different antigen specific antibodies separately immobilized to defined areas on the solid phase, followed by indirectly detecting the presence of bound antigen by titrating the unbound immobilized antibodies with a titrating antibody which is specific for the first antibody. This assay allows the simultaneous detection of a multiplicity of antigens in a single assay.

10 Claims, 11 Drawing Sheets

MULTIPLE ANTIGEN IMMUNOASSAY

This application is a continuation of application Ser. No. 049,375, filed May 14, 1987, now abandoned.

FIELD OF THE INVENTION

The invention relates to a method for the assay of an analyte which may be present in a sample by reacting a sample suspected of containing said analyte with antibodies immobilized to a solid support to form an antibody-antigen complex, followed by titrating the unoccupied antibody with a second labeled antibody which is specific to the first immobilized antibody, followed by detecting the label.

BACKGROUND OF THE INVENTION

The detection and quantitation of antigenic substances in biological samples frequently utilize immunoassay techniques. These techniques are based upon the formation of a complex between the antigenic substance being assayed and an antibody or antibodies in which one or the other member of the complex may be detectably labeled. With competitive immunoassay techniques, the antigenic substance in a sample fluid being tested competes with a known quantity of labeled antigen for a limited quantity of antibody binding sites. The amount of labeled antigen bound to the antibody is inversely proportional to the amount of antigen in a sample.

By contrast, most immunometric assays employ a labeled antibody. In such an assay, the amount of labeled antibody associated with the complex is directly proportional to the amount of antigenic substance in a fluid sample.

In sandwich immunometric assays, a quantity of unlabeled antibody is bound to a solid support which is insoluble in the fluid being tested. This immobilized antibody is first contacted with the sample being tested so that a binary antigen-antibody complex is formed. After a suitable incubation period, the solid support is washed to remove unbound antigens, then contacted with a solution containing a known quantity of a second antibody. After a second incubation period, the solid support is then washed a second time to remove the unreacted antibody. A labeled anti-antibody to the second antibody is then added, allowed to incubate for a sufficient amount of time, and the complex then washed. The washed solid support is then tested to detect and quantify the presence of labeled antibody, for example by measuring the emitted radiation of a radioactive label. The amount of labeled antibody detected is compared to that for a negative control sample. This type of assay is frequently referred to as a two-site or sandwich assay, since the antigen has two antibodies bonded to its surface at different locations. Despite their great utility, sandwich immunoassay has been recognized to be a slow procedure, in part because washing steps are required and lengthy incubation periods are required to reach equilibrium. David, et al., U.S. Pat. No. 4,376,110.

To eliminate at least one of the washing steps associated with this procedure, so-called simultaneous and reverse assays have been developed. A simultaneous assay involves a single incubation step as the antibody bound to the solid support and the labeled antibody are both added to the sample being tested at the same time. After incubation, the solid support is washed to remove unbound analyte and unbound antibody, and the bound antibody-analyte-labeled antibody "sandwich" is detected as with a conventional "forward" sandwich assay. A reverse assay involves the stepwise addition first of a solution of labeled antibody to the fluid sample followed by the addition of unlabeled antibody bound to a solid support after a suitable incubation. After a second incubation, the solid phase is washed in conventional fashion and the amount of labeled complex is detected as before. U.S. Pat. No. 4,098,876 to Piasio, et al. However, all of these methods suffer from the requirement for two antigen-specific antibodies which are able to recognize separate and distinct epitopes on an antigen. This is a critical limitation which makes the application of such immunoassays impractical for small antigens.

Immunoassays which require only one antigen-specific antibody are preferred. Such an immunoassay was described by Hirano, K. et al., *Anal. Biochem.* 154:624-631 (1986) who disclose an assay for tumor-specific alkaline phosphatase using a nitrocellulose filter coated with monoclonal antibodies specific for alkaline phosphatase. The presence of the bound analyte was determined by taking advantage of the enzymatic activity of the bound analyte. Thus, this type of immunoassay can only be used for detecting analytes with enzymatic activity which is stable to the conditions of the assay protocol. In addition, such assays are not applicable to detection of all enzymes. For example, enzymes such as thiol protease require the addition of reducing agents to stabilize them. Such reducing agents destroy antibodies by cleaving disulfide bonds.

A dot-blot assay for the detection and quantitation of the Leishmania glycoconjugate was developed which involves dot-blotting the solubilized protein from parasites onto nitrocellulose, blocking the free protein-binding sites with BLOTTO (5% w/v skim-powdered milk) and detecting the presence of the glycoconjugate with an iodinated monoclonal antibody. Handman, E. et al., *J. Immunol. Meth.* 83:113-123 (1985). A second two-site immunoradiometric assay disclosed by Handman for glycoconjugate involved immobilization of monoclonal antibody on nitrocellulose, blocking remaining protein binding sites with BLOTTO, binding with antigen, followed by a second incubation with the same monoclonal antibody, which was radioiodinated. This assay was based on the fact that Leishmania glycoconjugate possesses a large number of epitopes recognized by the monoclonal antibody. This suggests that Leishmania glycoconjugate contains a repetitive polymeric structure. Handman, supra. Thus, this immunoassay is limited to antigens capable of binding two or more identical antibodies. In addition, assays which rely on radioiodinated monoclonal antibody are relatively expensive because of the high costs of monoclonal antibodies and the limited shelf lives of most labeled antibodies.

Another immunoassay which involves a single antibody comprises immobilization of a monoclonal antibody on nitrocellulose, blocking the additional binding sites, and using a labeled antigen to detect the desired antibodies. Suresh, M. R. et al., *Anal. Biochem.* 151:192-195 (1985). This method is used to screen hybridoma supernatants and to detect monoclonal antibodies. However, in many instances, the antigen is not available in sufficient quantities to allow labeling for use in such an assay. Further, labeling the antigen can result in deleterious alteration of the immuno-specificity of the antigen.

U.S. Pat. No. 4,279,885 to Reese et al., describes a solid phase competitive protein binding assay where an antigen or hapten can be assayed. The method involves competition between the analyte and a labeled form thereof for a limited number of receptor or binding sites which are immobilized to a solid support. The assay may be conducted by mixing the components simultaneously or sequentially. The sequential assay involves contacting a solution of an analyte with a support containing immobilized receptors or antibodies, followed by contacting the mixture with a tracer. The tracer may be the analyte, or analog thereof, which contains a label or tag. Competitive assays are generally recognized to be less preferable to non-competitive assays.

It is also possible to have assays which do not utilize antibodies at all. For example, a sample containing protein to be assayed is mixed with a marker protein in contact with a polystyrene latex. A competition is created between the marker enzyme and the analyte protein for the limited surface binding sites. The inactivation of the enzyme upon binding to the hydrophobic latex surface allows measurement of the bound/free enzyme ratio, and thus, the competing protein concentration. However, this method is not able to distinguish between different proteins, and only gives a measure of the total protein content. Sandwick, et al., *Anal. Biochem.* 147:210-216 (1985).

Further improvements to immunoassay techniques involve the use of amplification strategies to increase the detection limit. These strategies include substrate cycling and enzyme channeling. Mosbach, K., *Ann. N. Y. Acad. Sci.* 434:239-248 (1984). However, neither system has been widely adopted.

Thus, it would be desirable to have an immunoassay which is fast and reliable, and requires the preparation of only one specific antibody. Further, it is desirable to have an immunoassay for a multiplicity of analytes utilizing one specific antibody for each analyte to effect detection.

SUMMARY OF THE INVENTION

The invention relates to a method for detecting and quantitating an analyte in a sample, which includes (a) contacting a sample suspected of containing the analyte with a solid phase support onto which an analyte-specific first antibody has been immobilized;

(b) incubating said sample with said support for a sufficient amount of time to allow the analyte present in the sample to bind to said first antibody;

(c) separating said solid support from the incubation mixture obtained in step (b);

(d) contacting said solid phase support with a detectably labeled titrating antibody which is specific for said first antibody;

(e) incubating the mixture formed in step (d) for a time sufficient to allow said titrating antibody to bind to said first antibody;

(f) separating said solid phase support from the incubation mixture obtained in step (e); and (g) detecting the analyte in the sample by measuring the amount of bound labeled antibody.

The invention relates as well to an assay for a multiplicity of analytes comprising contacting a sample suspected of containing a multiplicity of analytes with a solid support containing different analyte-specific antibodies separately immobilized onto defined areas of the solid phase support, followed by titration and detection with a common titrating antibody.

The invention also relates to a kit for the detection of an analyte in a sample comprising a carrier being compartmentalized to receive in close confinement therein one or more containers wherein (a) a first container contains a solid support containing a first antibody immobilized to said solid support wherein said first antibody is specific to an analyte;

(b) a second container contains washing buffers; and (c) a third container contains a titrating antibody specific for the first immobilized antibody.

The invention also relates to a kit for the detection of a multiplicity of analytes in a sample which includes a carrier means being compartmentalized to receive in close confinement therein one or more containers wherein (a) a first container contains a solid support containing a multiplicity of analyte-specific first antibodies separately immobilized to separate defined areas of said solid support;

(b) a second container contains washing buffers; and (c) a third container contains a second titrating antibody specific for each analyte-specific first antibody.

The invention offers a convenient, flexible and rapid method to detect and quantify one or more analytes in solution. In addition, the invention provides for recycling the solid phase support by elution with a chaotropic salt. Thus, the solid phase support may be reused and the antigen recovered from the assay system.

DESCRIPTION OF THE PREFERRED EMBODIMENTS

Figure 1:
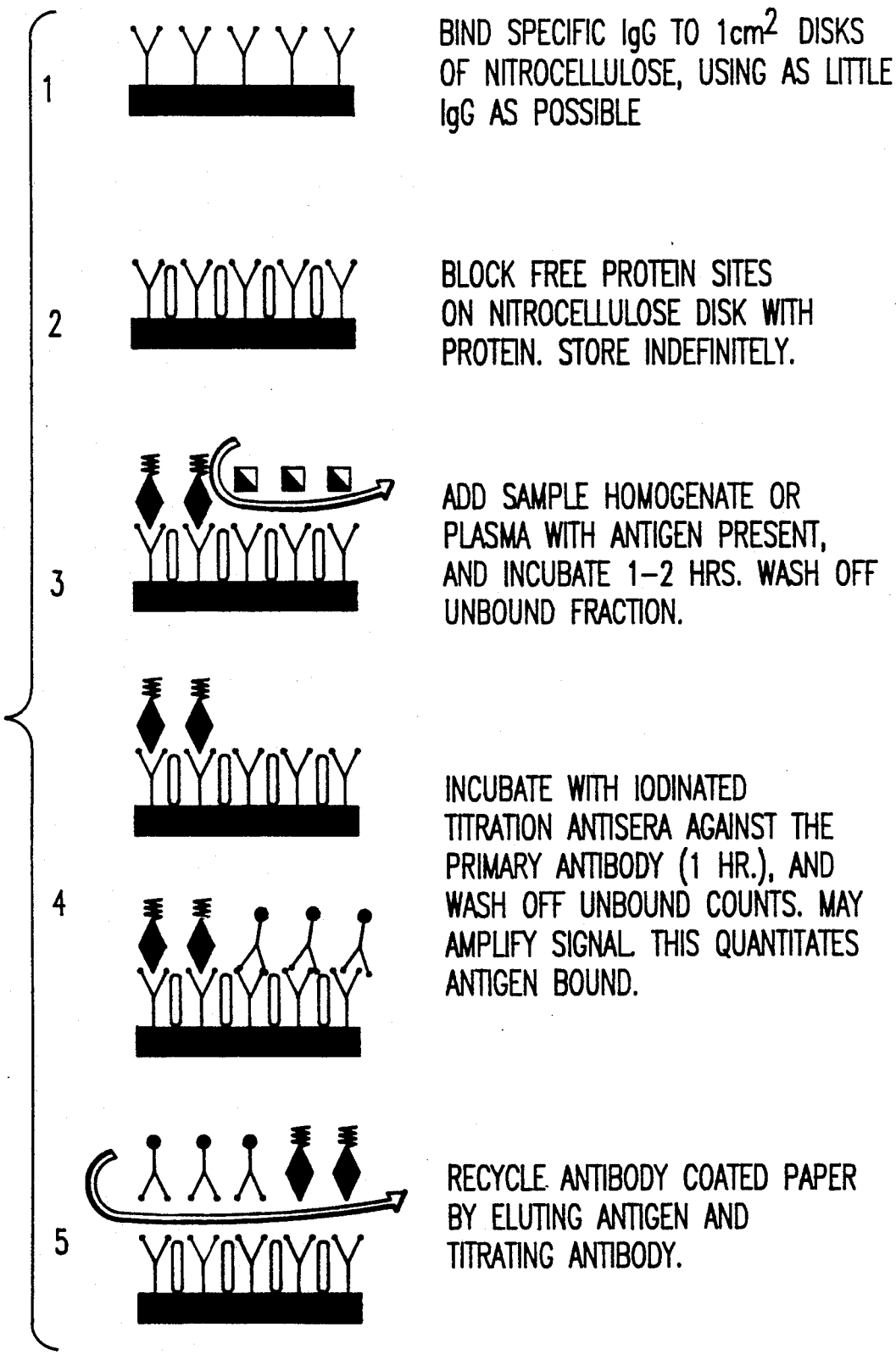
FIG. 1. This figure shows the general scheme of the assay, the titration of immobilized IgG not bound to antigen by iodinated IgG-specific antibody, and subsequent recycling of the nitrocellulose disk.

This invention is directed towards methods of assay by immobilizing a first antibody specific to an analyte on a solid phase support, contacting the sample suspected of containing the analyte with the immobilized antibody, and titrating the unbound antibody with a second labeled antibody which is specific for the first immobilized antibody.

By "solid phase support" is intended any support capable of binding antibodies. Such supports include but are not limited to nitrocellulose, diazocellulose, microtiter plates, glass, polystyrene, polyvinylchloride, polypropylene, polyethylene, dextran, affinity support gels such as Sepharose or agar, starch, and nylon. Preferred supports are nitrocellulose and diazocellulose. Those skilled in the art will note that many other suitable carriers for binding monoclonal antibody exist, or will be able to ascertain the same by use of routine experimentation.

The term "antibody" refers both to monoclonal antibodies which have a substantially homogeneous population and to polyclonal antibodies which have heterogeneous populations. Both the first and second antibodies may be monoclonal or polyclonal. Polyclonal antibodies are derived from the antisera of animals immunized with the analyte. Monoclonal antibodies to specific antigens may be obtained by methods known to those skilled in the art. See, for example Kohler and Milstein, Nature 256:495–497 (1975). Such antibodies may be of any immunoglobulin class including IgG, IgM, IgE, IgA, IgD and any subclass thereof.

The term "antibody" is meant as well to include both intact molecules as well as fragments thereof, such as, for example, Fab and F(ab′)$_2$, which are capable of binding antigen.

By the term "analyte" is intended any molecule with an antigenic site capable of binding to an antibody. Such analytes may include but are not limited to proteins, drugs, viruses, cells, haptens, subcellular particles, carbohydrates, hormones, vitamins, metabolites and their binding materials.

In one embodiment, the first analyte-specific antibody is a polyclonal antibody derived from an animal immunized with the analyte. The second titrating antibody may be heterologous polyclonal antibodies which are specific against the immunoglobulins comprising the first antibody. The second antibody may be obtained by isolating the antibodies from a second animal species which has been immunized with antisera from the same species of animal used to prepare the first antibody.

In another embodiment, a first IgG monoclonal antibody which is specific to the analyte to be assayed is used. The second titrating antibody comprises a detectably labeled anti-IgG polyclonal antibody specific to the first antibody.

In still another embodiment, a first IgG polyclonal antibody, which is specific to the analyte to be assayed, is used. The second titrating antibody comprises a detectably labeled anti-IgG monoclonal antibody specific to the first antibody.

In a preferred embodiment, a number of different analyte-specific antibodies derived from the same animal species may be separately immobilized on defined areas of a solid support which is attached to a dip stick. Thus, the dip stick may be incubated with a sample to assay for many different analytes simultaneously. The unoccupied antibody sites on each defined area can then be titrated with common titrating antibodies which are specific for each antigen-specific antibody. For instance, each analyte-specific antibody may be of the IgG class. The common titrating antibodies will then be anti-IgG antibodies. As used herein, the term "common titrating antibodies" is used in the plural, although it will be understood that only one class of antibodies is intended. This aspect of the invention provides for the simultaneous detection and quantitation of a multiplicity of antigens by a universal labeling method.

The amount of bound analyte is determined indirectly by measuring the amount of label associated with the second antibody which binds to the unoccupied first antibody. The amount of analyte present in a sample is inversely proportional to the amount of label present. There are many different labels and methods of labeling known to those of ordinary skill in the art. Examples of the types of labels which can be used in the present invention include, but are not limited to, enzymes, radioisotopes, dyes, fluorescent compounds, chemiluminescent compounds, bioluminescent compounds and metal chelates. Those of ordinary skill in the art will know of other suitable labels for binding to the antibody, or will be able to ascertain the same by the use of routine experimentation. Furthermore, the binding of these labels to the antibodies can be accomplished using standard techniques commonly known to those of ordinary skill in the art.

One of the ways in which the titrating antibody of the present invention can be detectably labeled is by linking the same to an enzyme. This enzyme, in turn, when later exposed to its substrate, will react with the substrate in such a manner as to produce a chemical moiety which can be detected as, for example, by spectrophotometric, fluorometric or visual means. Examples of enzymes which can be used to detectably label the antibody of the present invention include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase. Avidin-biotin binding may be used to facilitate the enzyme labeling.

The titrating antibody of the present invention can also be labeled with a radioactive isotope which can then be determined by such means as the use of a gamma counter or a scintillation counter. Isotopes which are particularly useful for the purpose of the present invention are: $^3H$, $^{125}I$, $^{131}I$, $^{32}P$, $^{35}S$, $^{14}C$, $^{51}Cr$, $^{36}Cl$, $^{57}Co$, $^{58}Co$, $^{59}Fe$ and $^{75}Se$.

It is also possible to label the titrating antibody with a fluorescent compound. When the fluorescently labeled antibody is exposed to light of the proper wave length, its presence can then be detected due to the fluorescence of the dye. Among the most commonly used fluorescent labelling compounds are fluorescein isothiocyanate, rhodamine, phycoerytherin, phycocyanin, allophycocyanin, o-phthaldehyde and fluorescamine.

The titrating antibody of the invention can also be detectably labeled using fluorescent emitting metals such as $^{152}Eu$, or others of the lanthanide series. These metals can be attached to the antibody molecule using such metal chelating groups as diethylenetriaminepentaacetic acid (DTPA) or ethylenediaminetetraacetic acid (EDTA).

The titrating antibody of the present invention also can be detectably labeled by coupling it to a chemiluminescent compound. The presence of the chemiluminescent-tagged titrating antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the titrating antibody of the present invention. Bioluminescence is a type of chemiluminescence found in biological systems in which a catalytic protein increases the efficiency of the chemiluminescent reaction. The presence of a bioluminescent antibody is determined by detecting the presence of luminescence. Important bioluminescent compounds for purposes of labeling are luciferin, luciferase and aequorin.

Another technique which may also result in greater sensitivity when used in conjunction with the present invention consists of coupling the titrating antibody of the present invention to low molecular weight haptens. The haptens can then be specifically detected by means of a second reaction. For example, it is common to use such haptens as biotin (reacting with avidin) or dinitrophenyl, pyridoxal and fluorescamine (reacting with specific antihapten antibodies) in this manner.

In addition, the sensitivity of the assay may be increased by use of amplification strategies including substrate cycling and enzyme channeling as taught by Mosbach, supra, incorporated by reference herein.

For the purposes of the present invention, the analyte which is detected by this assay may be present in a sample solution. Normally, the sample is a biological sample such as, for example, saliva, cerebrospinal fluid, blood, serum, urine, water, food and the like. However, the invention is not limited to assays using only these samples, it being possible for one of ordinary skill in the art to determine suitable conditions which allow the use of other samples. For instance, various chemicals and drugs are also capable of being antigens, and thus may be suitable assayed in water, food, or other samples by the methods of this invention.

In carrying out the titrating immunoassay of the present invention on a sample containing a multiplicity of analytes, the process comprises:

a) contacting a sample suspected of containing a multiplicity of analytes with a solid support on which different analyte-specific first antibodies have been separately immobilized to separately defined areas of said solid support:

b) incubating said sample with said support for a sufficient amount of time to allow the analytes present in the sample to bind to said first antibodies;

c) separating the solid phase support from the incubation mixture obtained in step b);

d) contacting said solid support with a detectably labeled titrating antibodies which are specific for said first antibodies;

e) incubating the mixture formed in step d) for a time sufficient to allow said titrating antibodies to bind to said first antibodies;

f) separating said solid phase support from the incubation mixture obtained in step e); and g) detecting the analyte in the sample by measuring the amount of bound labeled titrating antibodies to each separately defined area.

Of course, the specific concentrations of label and analyte, the temperature and time of incubation, as well as other assay conditions may be varied, depending on various factors including the concentration of antigen in the sample, the nature of the sample, and the like. Those skilled in the art will be able to determine operative and optimal assay conditions for each determination by employing routine experimentation. In addition, the eluted titrating antibody may be separated from the eluted analyte according to means known in the art and also recycled for reuse in the assay. The eluted analyte may further be recovered.

Detection of the labeled antibody may be accomplished by a scintillation counter, for example, if the label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with standards.

Other such steps as washing, stirring, shaking, filtering and the like may of course be added to the assays as is customary or necessary for the particular situation.

The solid phase immunosorbent may be recycled by elution of the antigen and the titrating antibody with a chaotropic salt such as $MgCl_2$. However, the invention is not limited to the use of $MgCl_2$, it being possible for one of ordinary skill in the art to determine other chaotropic salts which may be used to recycle the solid phase immunosorbent, without undue experimentation. In addition, the eluted titrating antibody may be separated from the eluted analyte according to means known in the art and may also then be recovered for re-use. The eluted analyte may further be recovered.

The assay of the present invention is ideally suited for the preparation of a kit. Such a kit may comprise a carrier means being compartmentalized to receive in close confinement therewith one or more container means such as vials, tubes and the like, each of said container means comprising the separate elements of the immunoassay. For example, there may be a container means containing the first antibody immobilized on a solid phase support, and further container means containing detectably labeled titrating antibodies in solution. Further container means may contain standard solutions comprising serial dilutions of analytes to be detected. The standard solutions of these analytes may be used to prepare a standard curve with the concentration of the analyte plotted on the abscissa and the detection signal on the ordinate. The results obtained from a sample containing an analyte may be interpolated from such a plot to give the concentration of the analyte.

In another embodiment of the kit, there may be a container means containing a dipstick which comprises a multiplicity of different analyte-specific antibodies separately immobilized to separate defined areas of the solid phase support. Further container means may contain a common titrating antibody which is specific for each analyte-specific antibody. Further container means may contain standard solutions of analytes to be detected. The standard solutions of these analytes may be used to provide a standard reference dipstick for comparison with the sample dipstick.

The various aspects of the invention are further described in the following examples. These examples are not intended to limit the invention in any manner.

EXAMPLES

EXAMPLE 1

General Procedure For the Immunoassay

In the examples that follow, a simple antibody-antigen system illustrates the protocol used for the assay for one antigen by isotopic detection.

Sheep anti-rabbit serum (SAR) was induced by sheep by standard procedures and heat inactivated at 56° C. for 30 minutes. Rabbit IgG was purchased from Sigma (St. Louis, Mo.). Iodination was achieved using iodo-beads (Pierce Chemical Company, Rockford, Ill.) using carrier-free sodium iodide-$I^{125}$ (Dupont New England Nuclear, Boston, Mass.). All other chemicals were reagent grade and were purchased from either Sigma Chemical Corporation (St. Louis, Mo.) or Fisher (Medford, Mass.).

Nitrocellulose paper (Millipore filter type HAHY 000-10, 0.45 uM pore size, Millipore Corporation, Bedford, Mass.) was used unless stated otherwise. The other papers tested include: Zeta Probe blotting membrane (cationized nylon, BioRad, Richmond, Calif.), mixed cellulose acetate and nitrate paper (GSWP 013-00, 0.22 uM pore size) and Millipore MF filters (HAWG04750, 0.45 uM pore size, Millipore Corporation, Bedford, Mass.), high binding capacity S&S Nytran (positively charged hydrophilic nylon-66, pore sizes 0.2 uM and 0.45 uM), S&S pure 100% hydrophilic nitrocellulose in different pore sizes (no cellulose acetate added, PH70, 0.025 uM pore size and BA83, pore size 0.2 uM, and BA85, pore size 0.45 uM, Schleicher and Schuell, Keene, NH), Hydrophilic Hybond-C 87 mm nitrocellulose and Hybond-N 132 mm nylon membranes (Amersham Corporation, Arlington Heights, Ill.).

Seven millimeter diameter disks of nitrocellulose (Millipore HA 0.45 uM pore, unless stated otherwise) were made using a standard office hole puncher and transferred by needle to a 15×75 millimeter polystyrene tube. Volumes between 50-300 ul of diluted antisera (SAR) were incubated with the disks at room temperature for 10 minutes. After washing in Tris-EDTA-azide, the samples were incubated in 1-2 ml of blocker. All titration and wash buffers utilized a base buffer of 50 mM Tris, 5 mM EDTA, 0.01% sodium azide at pH 7.4. Blocking buffers included 10% (v/v) bovine serum, 3% BSA, or 5% Carnation nonfat milk. The antigen (rabbit IgG) was then added (50-300 ul) and incubated for 30-60 minutes, as indicated in the following Examples. After washing three times, iodinated non-immune rabbit serum (NIRS-$I^{125}$) was added (50-300 ul) for the time stated (30 minutes minimum). After a second wash, the samples were counted for gamma radiation on a 40% efficient Packard Auto-Gamma Scintillation Spectrophotometer Model 5220.

EXAMPLE 2

The Efficiency of IgG Immobilization

The efficiency of IgG immobilization on nitrocellulose disks was determined as follows. Serial dilutions of SAR were incubated with a nitrocellulose disk. The nitrocellulose filter were then washed and titrated with iodinated antisera. A plot of the amount of bound IgG, as represented by the amount of radioactivity, appears schematically in the inset to FIG. 2. The competition between IgG and the larger proportion of other serum proteins for protein binding sites on nitrocellulose results in the affinity displacement (A) of IgG at high serum concentrations. As the antiserum concentration diminishes, the amount of immobilized IgG increases until the inflection point (X) is reached, where all the sample protein is absorbed equally. Diminishing concentrations of IgG beyond the inflection point are then reflected by diminishing counts of titrating antibody (B).

Figure 2:
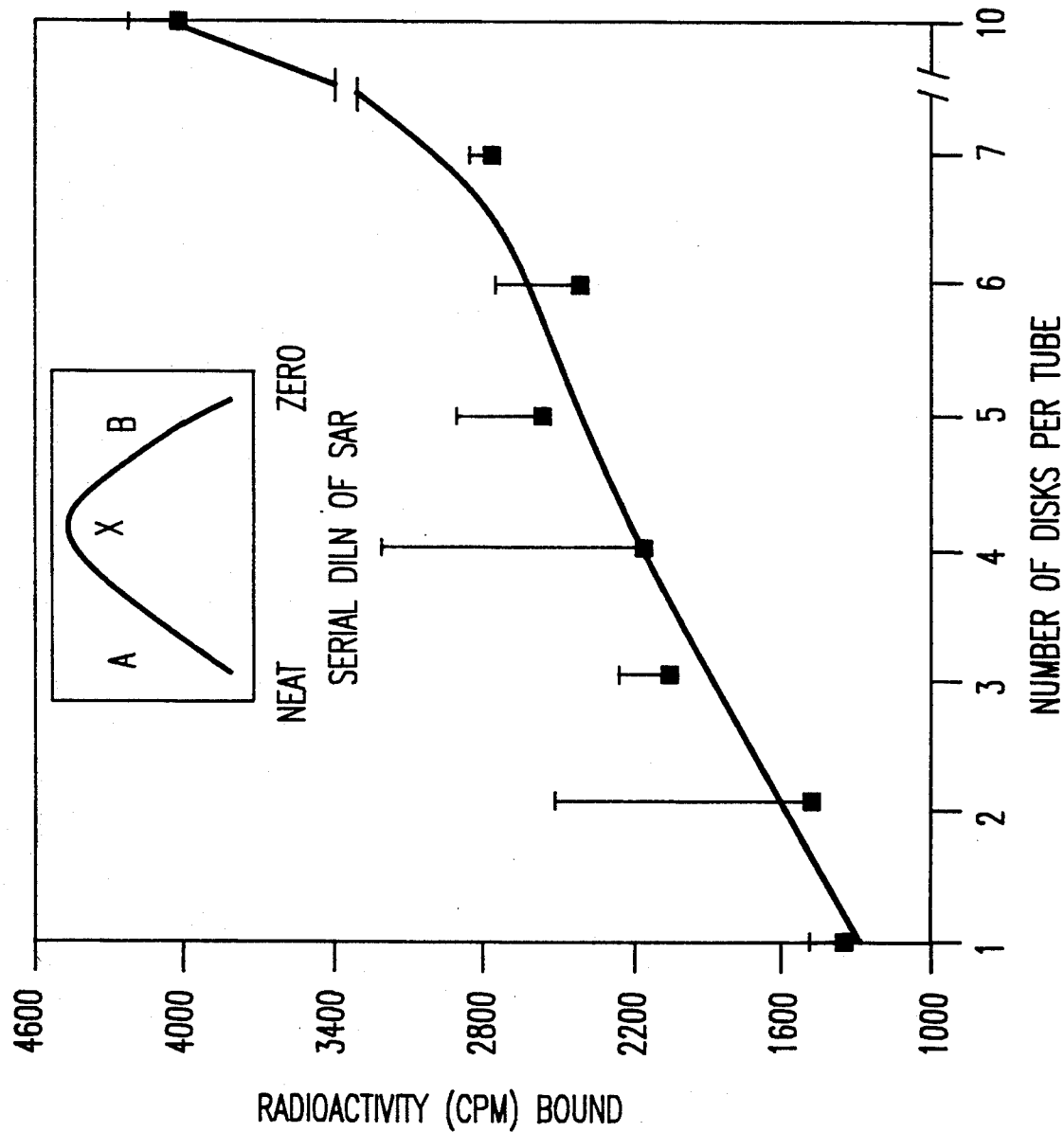
FIG. 2. This figure is a plot of the number of disks per tube versus the amount of bound radioactivity.

This inflection point can be displaced to higher serum concentrations if desired simply by providing more nitrocellulose binding sites. FIG. 2 shows the relationship between the number of nitrocellulose disks and the amount of bound radioactivity. 500 uL of sheep anti-rabbit serum was incubated for 10 minutes with 1-10 disks as shown in FIG. 2, washed with Tris buffer, blocked with 1 ml of 10% bovine serum blocker for 20 minutes, washed, titrated with 1 ml of NIRS-$I^{125}$ for 60 minutes, washed, and the radioactivity bound to the disk determined. At a tenfold increase in nitrocellulose surface area, the number of binding sites was no longer limiting for that concentration of sample. This illustrates that it is advantageous to use dilute sera for coating the matrix. Alternatively, purified IgG may be used to achieve high coating densities.

EXAMPLE 3

Stability of the Immobilized IgG

Figure 3:
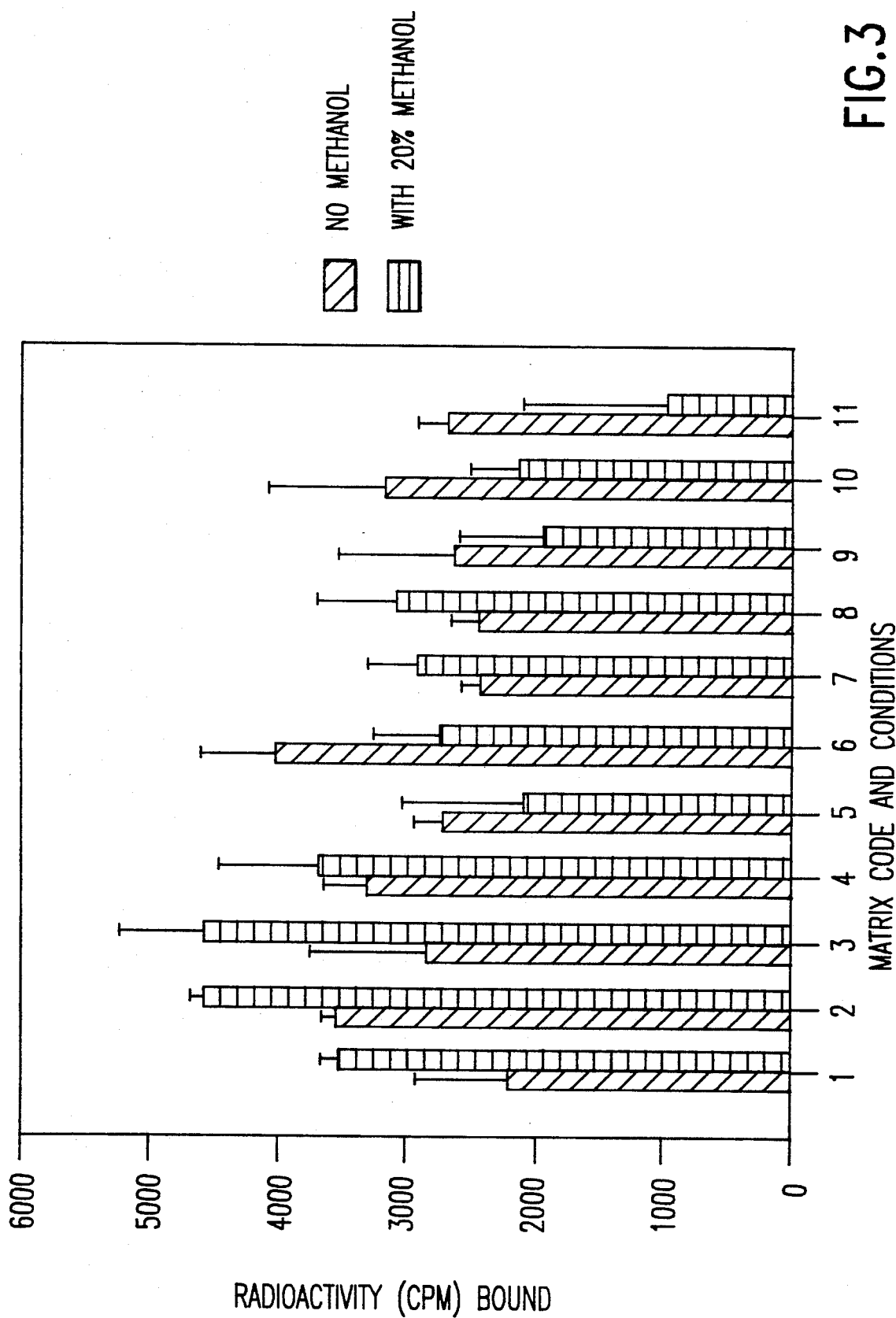
FIG. 3. This figure shows a comparison of the binding of iodinated sheep anti-rabbit (SAR) antibodies onto different types of immobilization matrices, with and without 20% methanol.
Figure 4:
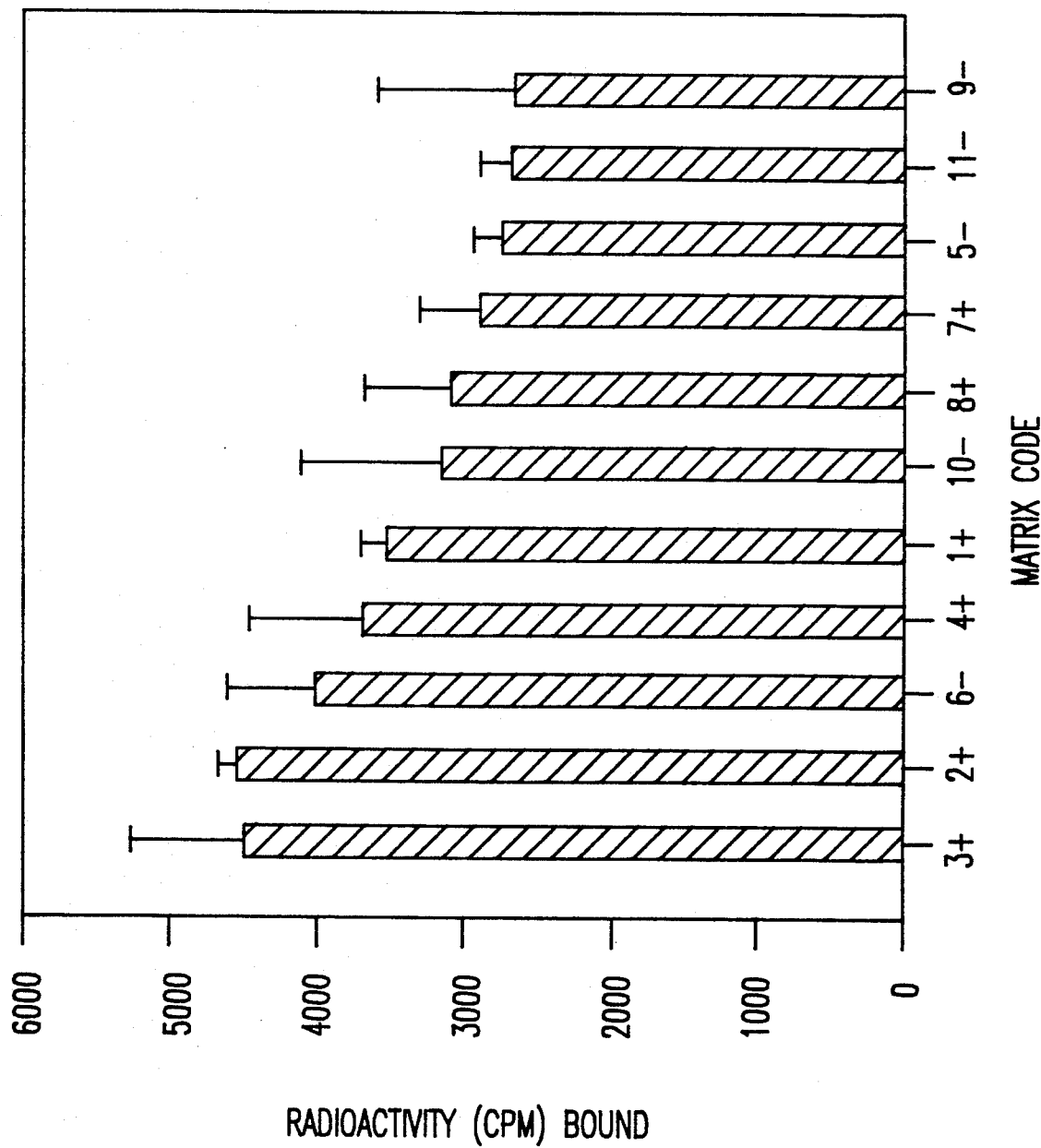
FIG. 4. This figure ranks the relative ability of different papers to absorb iodinated SAR with or without 20% methanol.

The stability of immobilized IgG on different immobilization matrices, with and without 20% methanol, was determined as follows. Disks of cellulose or nylon papers were incubated with iodinated SAR in Tris-EDTA for 20 minutes, with or without 20% methanol. The disks were then washed with Tris-EDTA and the radioactivity bound to the disks measured. The following papers were tested: 1) BioRad Zeta Probe, 2) Millipore nitrocellulose HA 0.45 uM pore, 3) Millipore mixed esters 0.22 uM pore, 4) Millipore MF 0.45 uM pore, 5) S&S Nytran 0.2 uM pore, 6) S&S 100% nitrocellulose 0.025 uM pore, 7) S&S Nytran 0.45 uM pore, 8) S&S 100% nitrocellulose, 0.2 uM pore, 9) S&S 100% nitrocellulose, 0.45 uM pore, 10) Amersham Hybond Nitrocellose, 11) Amersham Hybond nylon. The amount of bound radioactivity is depicted in FIG. 3. The relative abilities of different papers to absorb iodinated SAR under the best conditions (with (+) or without (−) 20% methanol) is depicted in FIG. 4. Millipore 0.45 uM pore nitrocellulose gave the best results and was chosen for all subsequent experiments. Mixed acetate paper also performed well despite reports in the literature that such papers poorly absorbed proteins (Gershoni, J. M., et al., *Anal. Biochem.* 131:1-15 (1983)). For S&S pure nitrocellulose paper, smaller pore sizes performed better (0.02 versus 0.45 uM).

Figure 5:
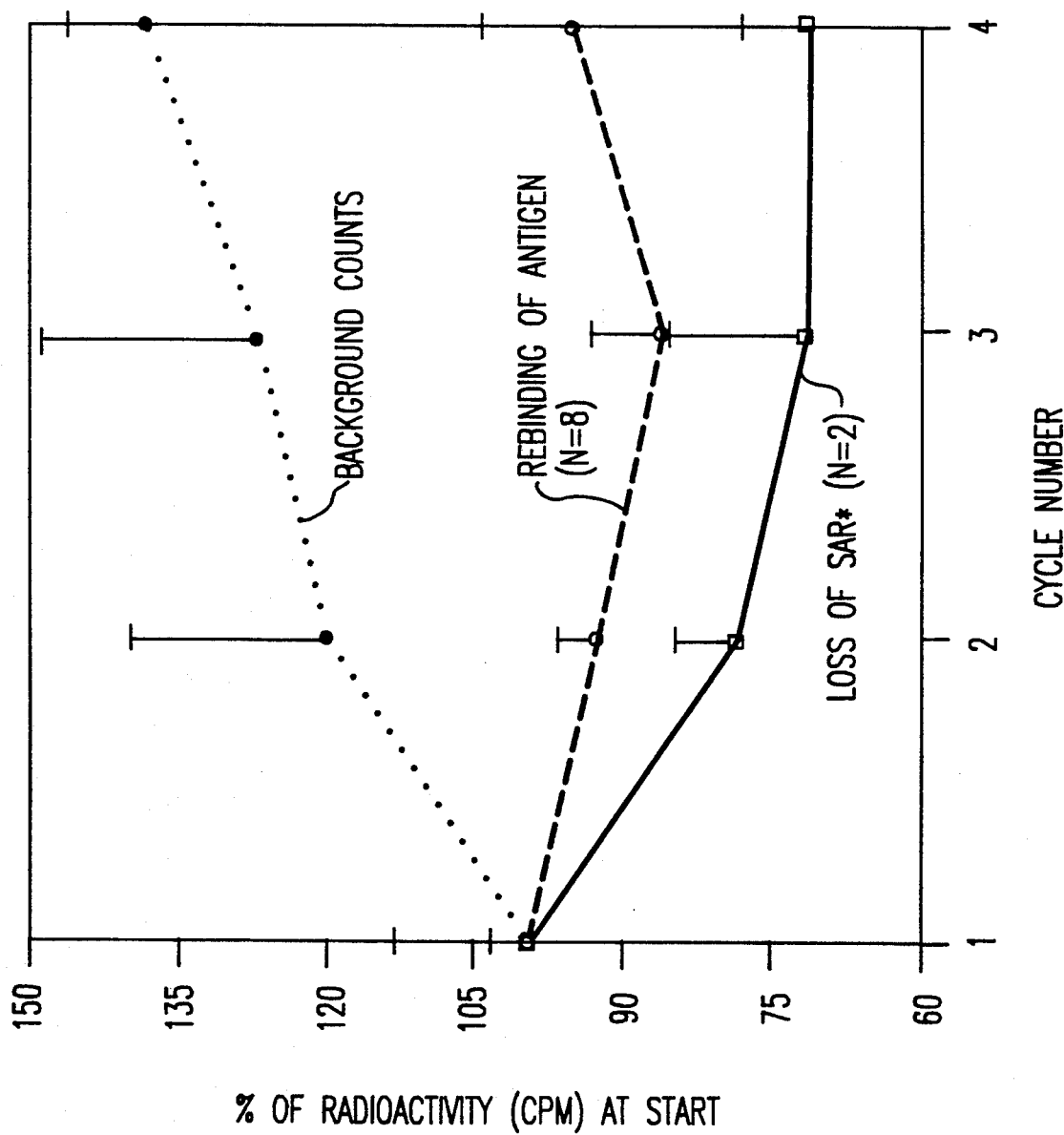
FIG. 5. This figure shows the effect of recycling antibody coated disks on the amount of residual radioactivity associated with the absorbed antibody.

The effect on stability of the immobilized IgG was then examined during recycling. Nitrocellulose disks in this experiment, were recycled four times. Nitrocellulose disks containing immobilized sheep anti-rabbit IgG and titrating antibody NIRS-$I^{125}$ were eluted with 2.5M $MgCl_2$ and the loss of antibody during the elution cycle determined. Four elutions with $MgCl_2$ resulted in a 20% loss of absorbed antibody (as determined by iodinated sheep anti-rabbit serum) as shown in FIG. 5. To test the functional integrity of the SAR remaining after each cycle of the elution, the disks were incubated with 150 uL of iodinated NIRS-antigen for 60 minutes, followed by washing in milk buffer, and counting the radioactivity remaining on the disk. Background counts were determined using the counts adhering after elution of the iodinated antigen. All data as shown in FIG. 5 is normalized as a percentage of the starting value. During regeneration cycles, nonspecific binding increased gradually, which indicates the absorption of label onto sites vacated by the blocker protein or the sheep anti-rabbit serum.

EXAMPLE 4

Optimization of Amounts of Immobilized IgG

Figure 6:
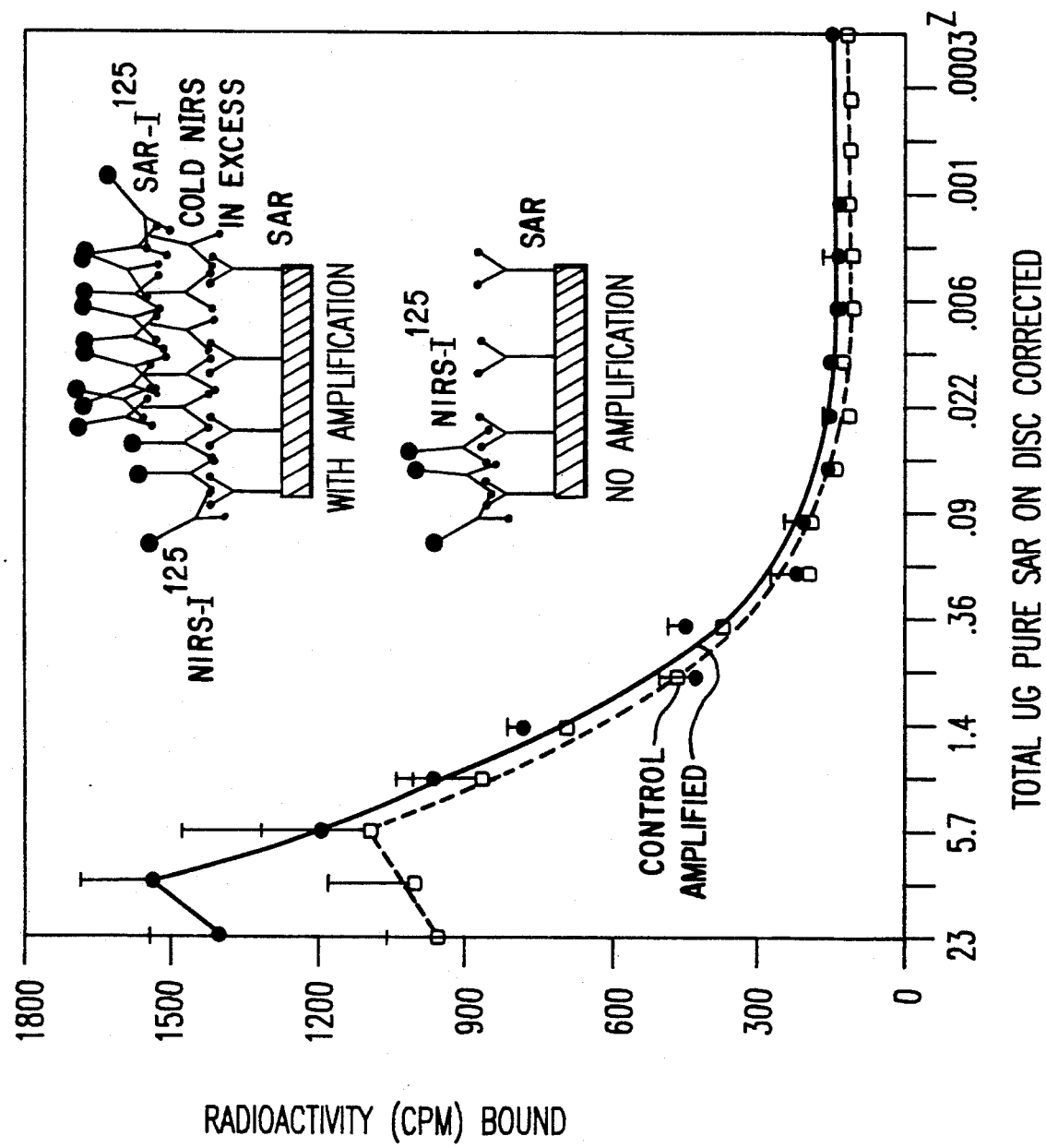
FIG. 6. This figure shows a standard curve for the titration of nitrocellulose-immobilized affinity purified SAR IgG immobilized onto nitrocellulose.

In this example, the amount of IgG necessary to give a readable signal was determined. Five ul aliquots of serial dilutions of SAR were spotted onto disks of nitrocellulose and dried. They were blocked for 30 minutes in 2 ml of 5% nonfat milk, washed in Tris-EDTA, and incubated with 150 ul of iodinated NIRS in 3% BSA for 60 minutes. Following thorough washing, the radioactivity bound to the disks was determined. As can be seen in FIG. 6, the lowest detectable amount of bound IgG under these conditions was approximately 25 ng. A parallel series of experiments were conducted by amplifying the detection signal with iodinated SAR. Again, the lowest detection limit was about 25 ng.

Figure 7:
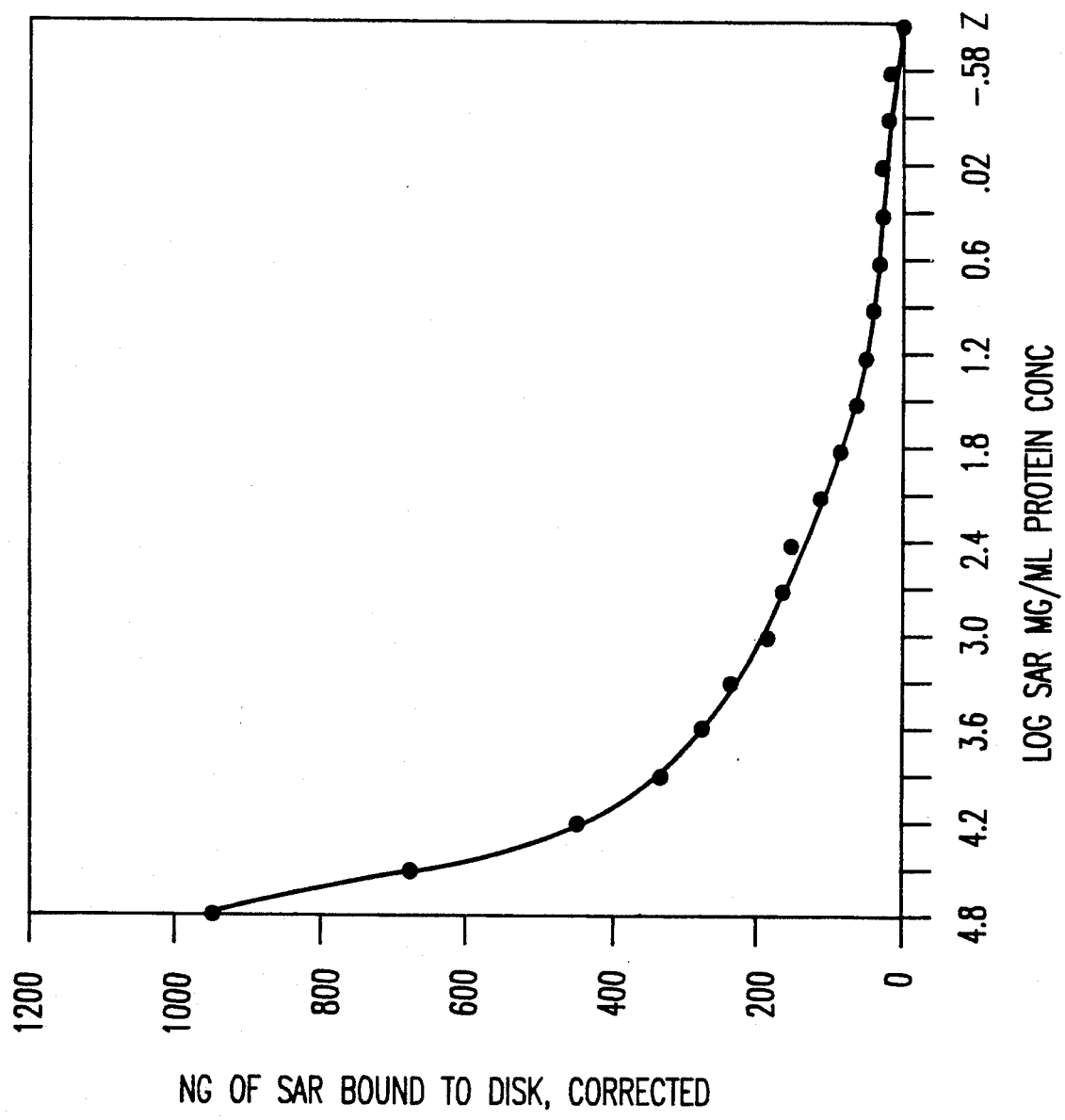
FIG. 7. This figure shows a determination of the amount of IgG bound to nitrocellulose disks for a range of different SAR dilutions.

The amount of IgG bound to the disks after brief incubation with a range of serum dilutions is depicted in FIG. 7. 100% efficient absorption was achieved at a titre of approximately 1:500. At lower dilutions, decreasing amounts of sample IgG were absorbed onto the matrix. The capacity of the nitrocellulose is approximately 80 ug/cm$^2$. The area of the disk used was about 1 cm$^2$. Thus, the amount of specific IgG is far short of saturating the disk. About 50% absorption of total sample IgG was achieved by using 1:128 dilution of serum.

EXAMPLE 5

Optimization of Incubation Time for Disk Coating

Figure 8:
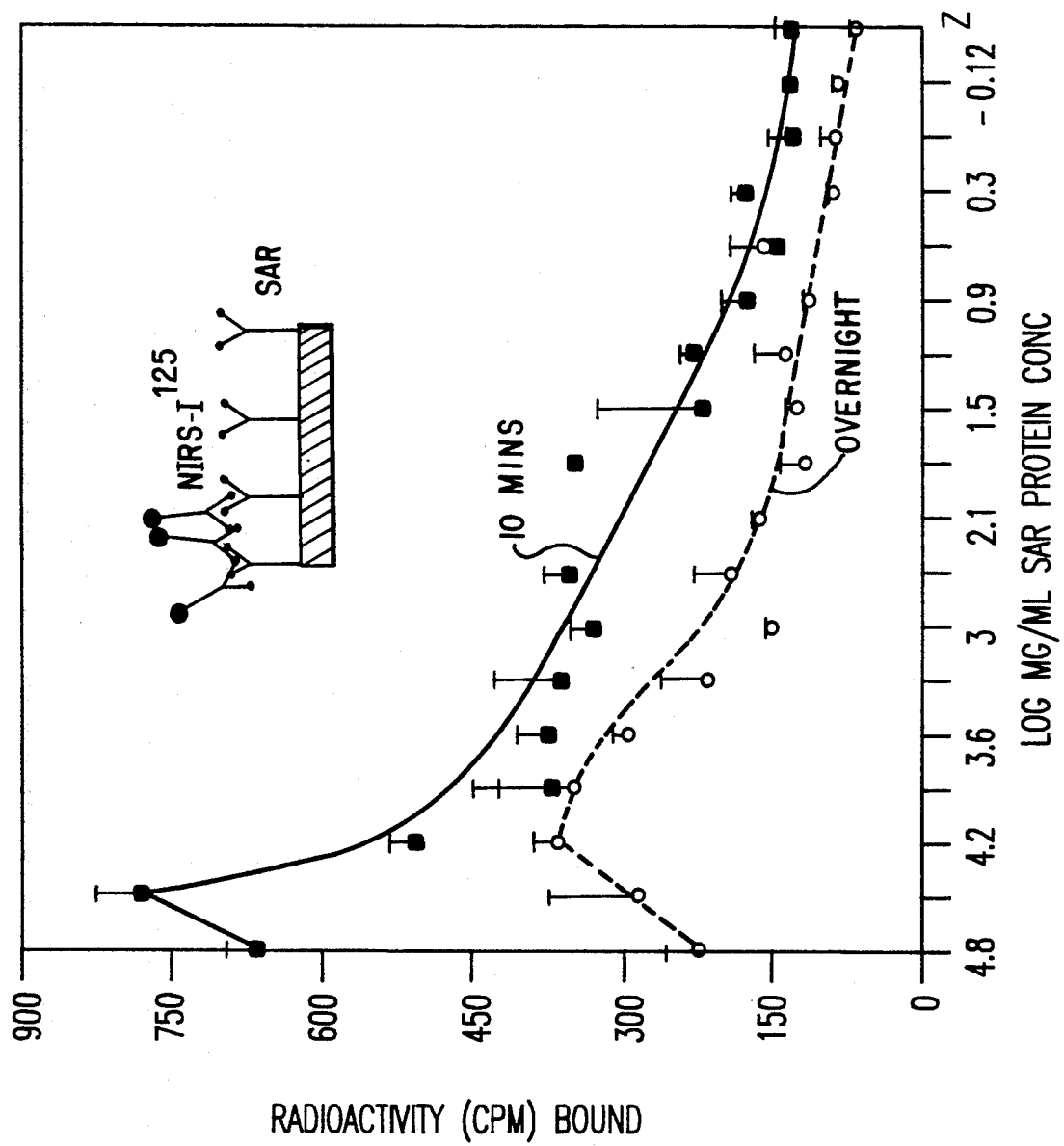
FIG. 8. This figure depicts a comparison of a 10-minute incubation with an overnight incubation for a series of SAR dilutions.
Figure 9:
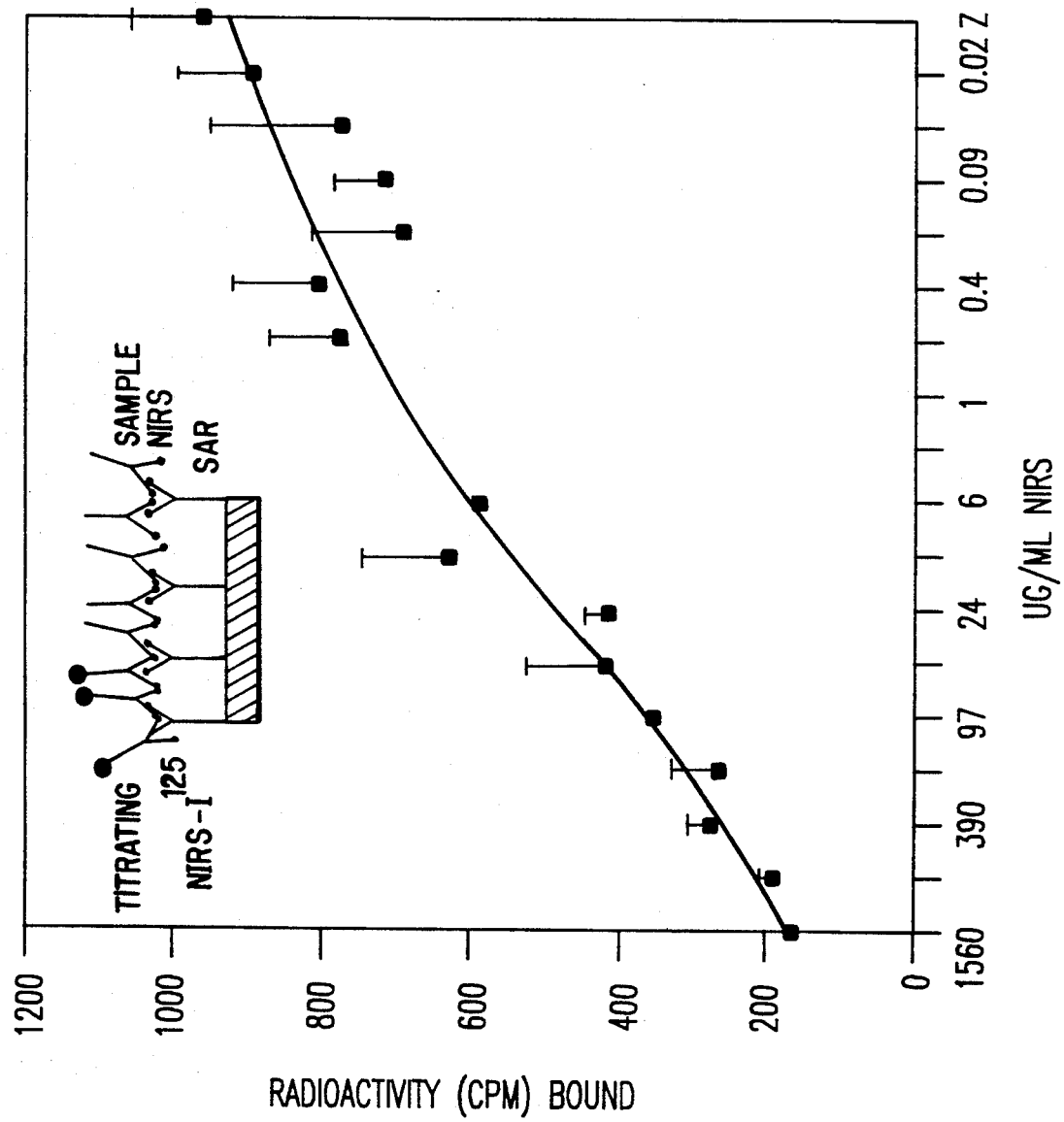
FIG. 9. This figure shows a standard curve for various concentrations of NIRS using SAR-coated nitrocellulose disks, obtained by titration of unbound free antibody sites with iodinated titrating antibody.

To achieve maximal immobilization of antisera, serial dilutions of SAR were incubated with nitrocellulose disks for 10 minutes or overnight. A comparison of a 10 minute incubation with an overnight incubation for a wide range of SAR dilutions is shown in FIG. 8. A 10-minute incubation bound more IgG than an overnight incubation. In addition, an overnight incubation showed an inflection point. The development of the inflection point only in the longer incubation time is due to the displacement of IgG by other serum proteins, due to either mass action or affinity differences. At all dilutions of SAR, the binding of IgG was diminished with the longer incubation time. After incubation, the samples were washed, blocked with 1 ml of 5% nonfat milk for 20 minutes, washed again and incubated with 450 ml of iodinated NIRS for 60 minutes in nonfat milk buffer. After thorough washing, the radioactivity bound to the disks was measured and is presented in FIG. 8. The relationship of the time of incubation for shorter time periods and the radioactivity bound to the disks appears in Table 1.

TABLE 1

| Time of incubation (minutes) | Radioactivity bound to disk SAR concentration | | |
|---|---|---|---|
| | Undiluted | 1:4 | 0 (blank) |
| 1 | 171 ± 20 | 158 ± 12 | 523 ± 2 |
| 5 | 155 ± 9 | 199 ± 16 | 984 ± 14 |
| 10 | 151 ± 33 | 171 ± 26 | 738 ± 13 |
| 20 | 162 ± 7 | 318 ± 159 | 1036 ± 136 |

TABLE 1-continued

| Time of incubation (minutes) | Radioactivity bound to disk SAR concentration | | |
|---|---|---|---|
| | Undiluted | 1:4 | 0 (blank) |
| 40 | 126 ± 4 | 172 ± 0 | 718 ± 147 |
| 130 | 146 ± 33 | 215 ± 57 | 1190 ± 8 |

Undiluted, 1:4, and samples with no SAR were spiked with iodinated SAR, and 100 ul incubated with each disk for the time shown. After washing with 2 ml volumes of 5% nonfat milk buffer, the counts remaining on the disks were determined. The total counts added initially were 3610+596. Thus, the percentage of the total that became bound ranged from 14% at one minute to 33% at 130 minutes. The counts are expressed as mean and SD of duplicates. Maximal binding of IgG in a 100 ul sample occurred at 20 minutes at a 1:4 dilution. However, this data was not significantly different from the 10 minute incubation. Table 2 depicts the percentage of total counts bound to the blank disk for each length of time. The binding plateaus between 10–20 minutes. Adequate coating of disks was achieved using 100 ul of SAR at a dilution of 1:200 for 10 minutes.

TABLE 2

| Time (minutes) | % of Total Counts Bound to Blank Disk |
|---|---|
| 1 | 14.5 ± 0.3 |
| 5 | 27.2 ± 2 |
| 10 | 20.4 ± 2 |
| 20 | 28.7 ± 13 |
| 40 | 19.9 ± 2 |
| 134 | 32.9 ± 0.6 |

Legend: Timecourse of SAR adsorption onto nitrocellulose disks. The data is derived from Table 1.

EXAMPLE 6

Optimization of Incubation Time With Titrating Antibody

Figure 10:
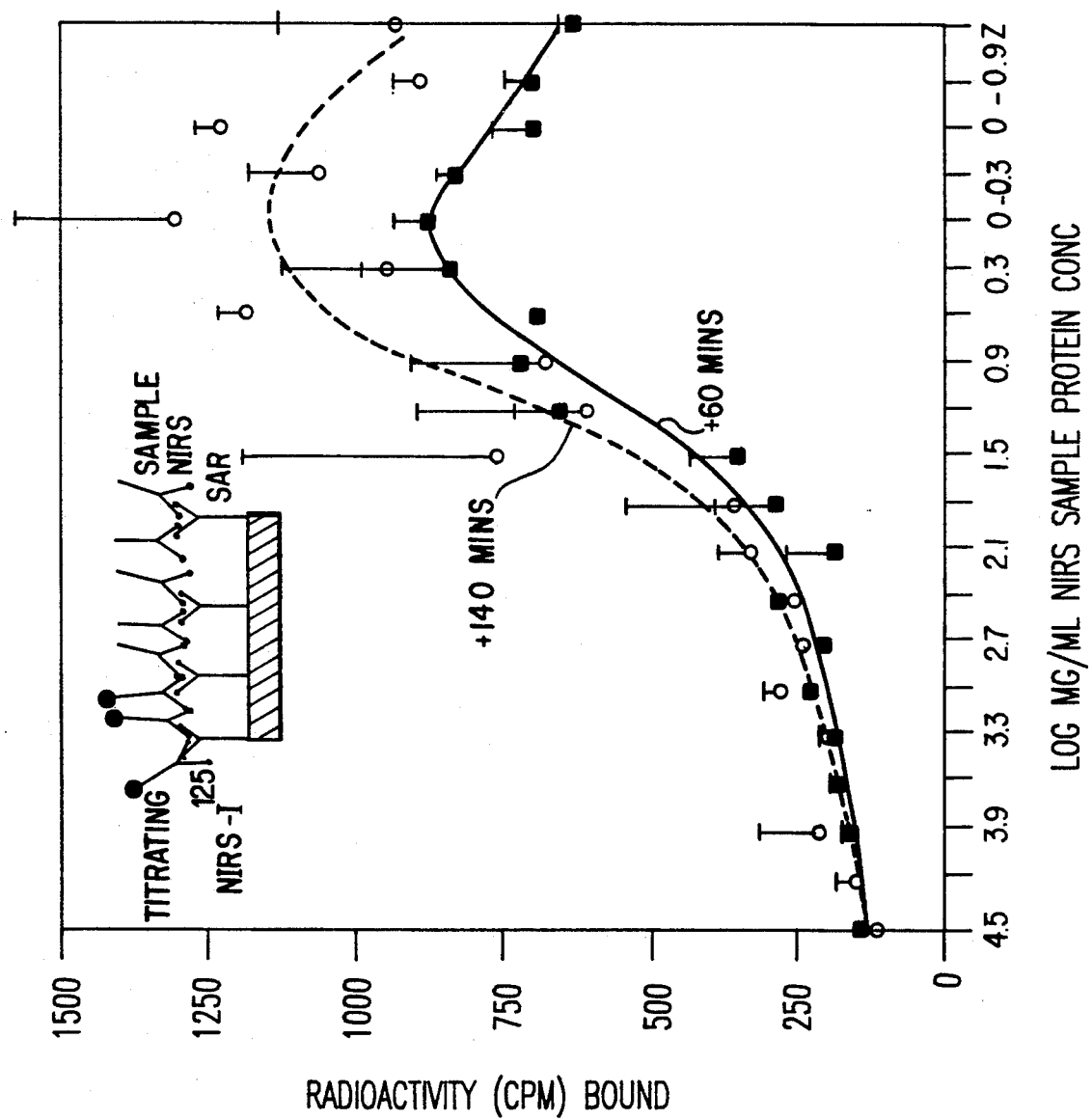
FIG. 10. This figure compares the amount of bound titrating antibody for two different incubation times and varying concentrations of NIRS.
Figure 11:
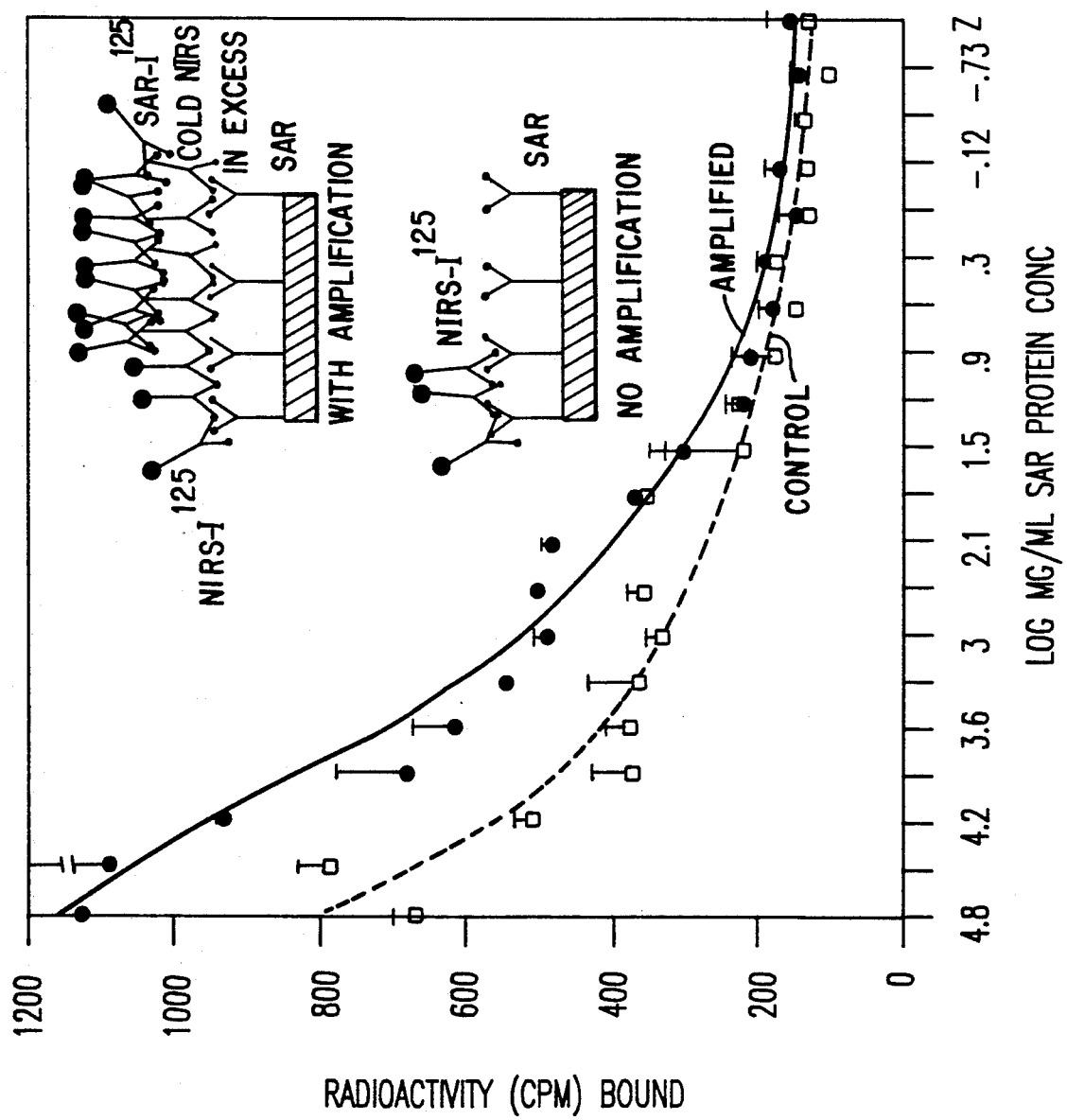
FIG. 11. This figure shows the effect of amplification of titrating antibody for different concentrations of SAR.

The relationship between the time of incubation of the titrating labeled antibody (60 or 140 minutes) and the amount of bound label for various serial dilutions of NIRS appears FIG. 10. The disks were coated with SAR at a 1:4 dilution (100 ul for 20 minutes), blocked for 20 minutes in 1 ml of 5% nonfat milk buffer, and incubated with 200 ul of serial dilutions of NIRS serum overnight at 4° C. After thorough washing, the free sites were titrated with 100 ul of iodinated NIRS for the time specified. After washing, the radioactivity bound to the disk was determined.

The 140 minute incubation did increase the amount of bound label and the amplitude of the signal, although the error bars were greater. This indicated that there was an increased amount of nonspecific binding with longer incubation times. The amplification was greatest at low concentrations of sample NIRS, where the number of free IgG binding sites was greatest. The titrating antibody may have a greater affinity for the immobilized IgG than the sample antigen.

EXAMPLE 7

Amplification by Two Iodinated Titrating IgG's

The effect of amplification of the signal was then examined. Antigen-free IgG molecules were incubated with iodinated NIRS followed by binding the remaining unbound IgG molecules with an excess of unlabeled anti-IgG molecules to provide a carpet for the subsequent binding of a second labeled anti-IgG molecule. Amplification occurs as a result of the ability of each immobilized primary antibody to bind to more than one labeled IgG molecule. This second layer of molecules allows a higher binding of a second labeled titrating antibody by virtue of mass action. Further, there is a higher probability of collision between the titrating IgG molecule and the "carpet" target IgG molecules than collision with primary immobilized antibody due to their number. Amplification resulted in an increase in the signal, especially where there was less antigen-bound IgG.

Having now fully described this invention, it will be appreciated by those skilled in the art that the same can be performed within a wide range of equivalent parameters and concentrations and conditions without departing from the spirit and scope of the invention or any embodiment thereof. The descriptions disclosed herein refer only to a model system. Any antibody-antigen combination may be determined by one of ordinary skill in the art without undue experimentation.

What is claimed is:

1. A method for determining the presence of an analyte in a sample, comprising:
   a) contacting a sample suspected of containing the analyte with a solid phase support onto which an analyte-specific first antibody has been immobilized;
   b) incubating said sample with said support for a sufficient amount of time to allow the analyte present in the sample to bind to said first antibody;
   c) separating said solid phase support from the incubation mixture obtained in step b);
   d) contacting said solid phase support with a second detectably labeled titrating antibody which is specific for said first antibody;
   e) incubating the mixture formed in step d) for a time sufficient to allow said titrating antibody to bind to said first antibody;
   f) separating said solid phase support from the incubation mixture obtained in step e); and
   g) detecting and measuring the amount of bound labeled antibody and correlating the amount of bound labeled antibody to the amount of analyte in the sample by comparing the amount of bound labeled antibody to a standard curve constructed from analyte standards, wherein the quantity of analyte is inversely proportional to the amount of bound labeled antibody.

2. The method of claim 1 wherein said solid phase support is selected from the group consisting of nitrocellulose, diazocellulose, microtitre plates, glass, polystyrene, polypropylene, polyethylene, dextran, Sepharose, agar, starch and nylon.

3. The method of claim 1, wherein said solid phase support is selected from the group consisting of nitrocellulose and diazocellulose.

4. The method of claim 1 wherein said detectable label is selected from the group consisting of a radioactive isotope, a dye, a fluorescent label, a bioluminescent compound, and an enzyme.

5. The method of claim 1 wherein said first antibody is of the IgM, IgA, IgD, IgE or IgG immunoglobulin class.

6. The method of claim 5 wherein said first antibody is of the IgG immunoglobulin class.

7. The method of claim 1, wherein said solid phase support is recycled after step g) and said analyte and titrating antibody recovered by elution with a chaotropic salt.

8. The method of claim 7, wherein said chaotropic salt is $MgCl_2$.

9. The method of claim 1, wherein said solid phase support contains a multiplicity of different analyte-specific first antibodies, each immobilized to separately defined areas and said second, detectably labeled titrating antibody is specific for each analyte-specific first antibody.

10. A method for determining the presence of a multiplicity of analytes in a sample, comprising:
   a) contacting a sample suspected of containing a multiplicity of analytes with a solid support on which different analyte-specific first antibodies have been separately immobilized to separately defined areas of said solid support;
   b) incubating said sample with said support for a sufficient amount of time to allow the analytes present in the sample to bind to said first antibodies;
   c) separating the solid phase support from the incubation mixture obtained in step b);
   d) contacting said solid phase support with second detectably labeled titrating antibodies which are specific for said first antibodies;
   e) incubating the mixture formed in step d) for a time sufficient to allow said titrating antibodies to bind to said first antibodies;
   f) separating said solid phase support from the incubation mixture obtained in step e); and
   g) detecting and measuring the amounts of bound labeled antibodies and correlating the amounts of bound labeled antibodies to the amount of each analyte in the sample by comparing the amounts of bound labeled antibodies to standard curves constructed from each of the analyte standards, wherein the quantity of analyte is inversely proportional to the amount of bound labeled antibody.

* * * * *